(12) United States Patent
Barron et al.

(10) Patent No.: US 9,612,202 B2
(45) Date of Patent: Apr. 4, 2017

(54) USE OF NANOPARTICLES IN THE PREPARATION OF CALIBRATION STANDARDS

(71) Applicant: REAGECON DIAGNOSTICS LTD, Shannon/Co Clare (IE)

(72) Inventors: John Barron, Ennis (IE); Vaclav Sychra, Prague (CZ); John O'Keeffe, Ennis (IE)

(73) Assignee: REAGECON DIAGNOSTICS LTD, Shannon/Co Clare (IE)

( * ) Notice: Subject to any disclaimer, the term of this patent is extended or adjusted under 35 U.S.C. 154(b) by 0 days.

(21) Appl. No.: 14/640,139

(22) Filed: Mar. 6, 2015

(65) Prior Publication Data

US 2015/0253249 A1 Sep. 10, 2015

(30) Foreign Application Priority Data

Mar. 7, 2014 (EP) .................................... 14158254

(51) Int. Cl.
| | | |
|---|---|---|
| *G01N 21/27* | (2006.01) | |
| *G01N 21/31* | (2006.01) | |
| *G01N 21/73* | (2006.01) | |
| *G01N 21/71* | (2006.01) | |
| *B82Y 15/00* | (2011.01) | |
| *G01N 15/10* | (2006.01) | |

(52) U.S. Cl.
CPC ........... *G01N 21/73* (2013.01); *G01N 21/278* (2013.01); *G01N 21/3103* (2013.01); *G01N 21/71* (2013.01); *B82Y 15/00* (2013.01); *G01N 2015/1018* (2013.01); *Y10T 436/101666* (2015.01)

(58) Field of Classification Search
CPC .................................................... G01N 21/278
See application file for complete search history.

(56) References Cited

U.S. PATENT DOCUMENTS

| | | |
|---|---|---|
| 8,673,053 B2 | 3/2014 | Lee et al. |
| 2003/0112431 A1 | 6/2003 | Ketkar |
| 2008/0233652 A1 | 9/2008 | Kreyenschmidt et al. |
| 2011/0076687 A1 | 3/2011 | Haberstroh et al. |
| 2011/0309311 A1 | 12/2011 | So et al. |

FOREIGN PATENT DOCUMENTS

| | | |
|---|---|---|
| EP | 2395346 | 12/2011 |
| WO | 2007056977 | 5/2007 |

OTHER PUBLICATIONS

European Search Report dated Aug. 26, 2014 corresponding to EP Application No. 14158254.4.

*Primary Examiner* — Paul Hyun
(74) *Attorney, Agent, or Firm* — Niels Haun; Dann, Dorfman, Herrell & Skillman, P.C.

(57) ABSTRACT

This invention concerns the use of nanoparticles comprising an analyte in the preparation of a calibration standard for use in an analytical atomic spectroscopic technique and a method of calibrating such an instrument.

13 Claims, 2 Drawing Sheets

Figure 1 :- ICP-OES Response for Example 1
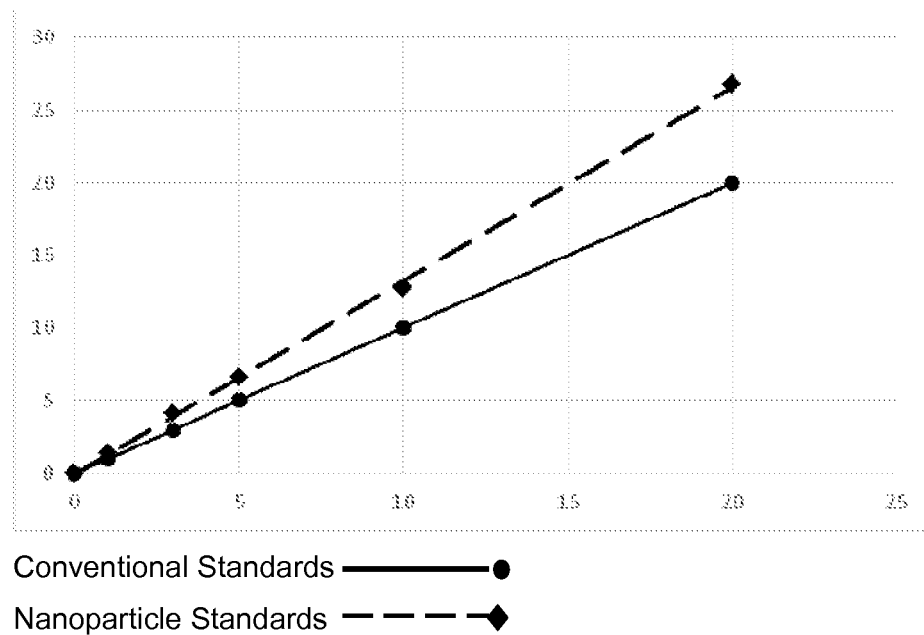
Conventional Standards ———●
Nanoparticle Standards — — — ◆
Figure 2 :- Nitrous Oxide-Acetylene Flame Response for Example 2
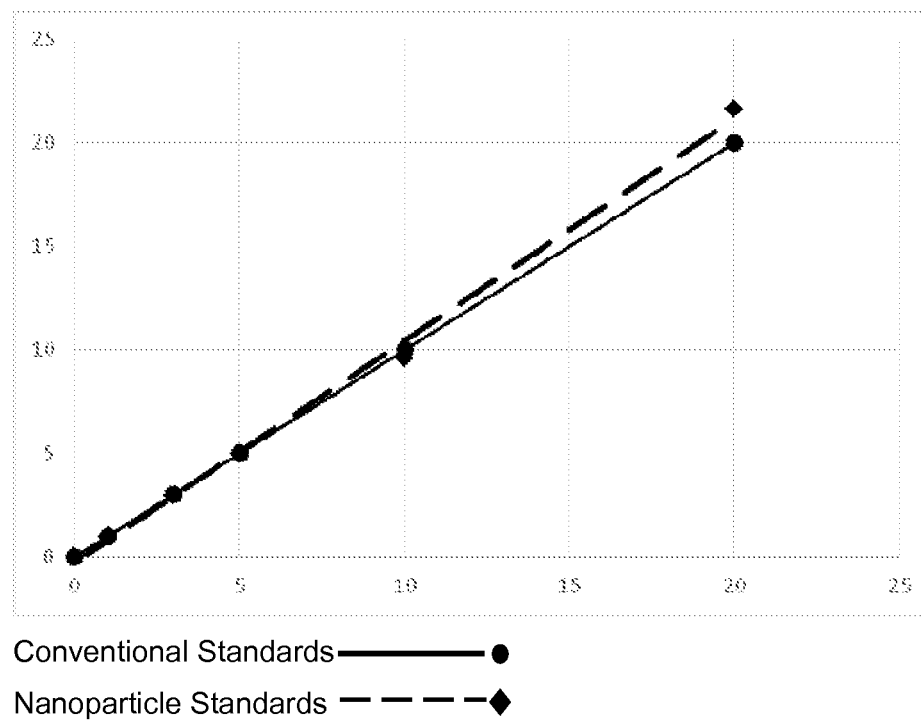
Conventional Standards———●
Nanoparticle Standards — — — ◆

Figure 3 :- ICP-OES Response For Example 3
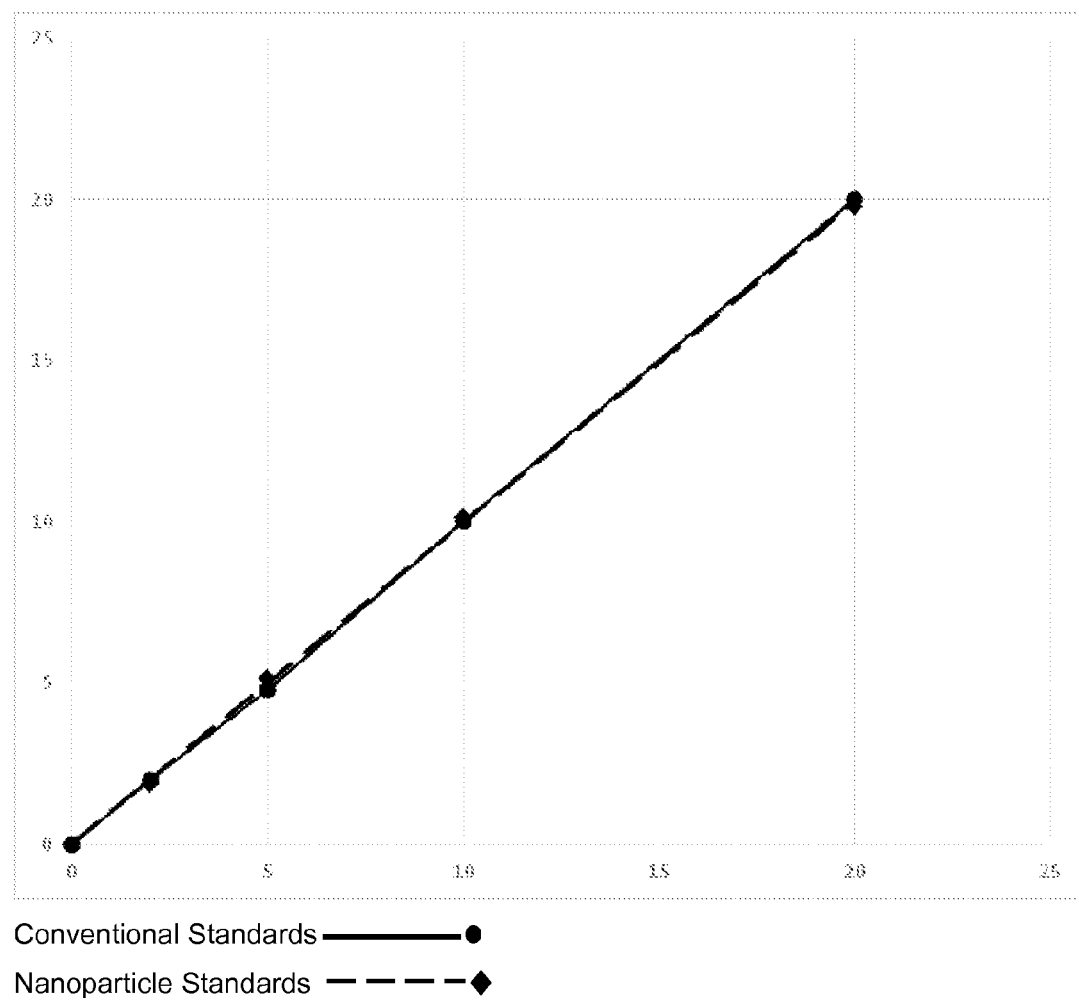
Conventional Standards ——————●
Nanoparticle Standards — — — —◆

USE OF NANOPARTICLES IN THE PREPARATION OF CALIBRATION STANDARDS

RELATED APPLICATIONS

This application claims the benefit of priority under 35 U.S.C. 119 of European Patent Application No. 14158254.4, filed on 7 Mar. 2014, the entire contents of which application(s) are incorporated herein by reference.

FIELD OF THE INVENTION

This invention relates to the use of nanoparticles in the preparation of calibration standards for use in analytical atomic spectroscopic techniques, such as flame and flameless AAS, AES, AFS, ICP-OES, ICP-MS, DCP, XRF and related techniques.

BACKGROUND OF THE INVENTION

In atomic spectrometric methods, the sample, usually in the form of solution, is aspirated by means of a pneumatic nebulizer into a spray chamber from which it passes in the form of fine aerosol into the atomizer (flame AAS) or into the emission (mass) source (ICP-OES, ICP-MS). First, desolvation takes place, i.e. solvent evaporates resulting in so called "dry aerosol" of small solid particles (microparticles, nanoparticles) e.g. salt crystals. These particles enter the atomizer and then undergo several thermal rearrangement reactions (melting, volatilization, dissociation, atomization, excitation, ionisation). The precise reactions that occur will depend on the atomizer temperature and reaction partners (flame gases, ions) generated in the atomizer (emission source) or from the sample matrix. For example, hydrated chlorides, formed by many elements from hydrochloric acid solutions, can form oxides under the elimination of hydrogen chloride. Oxides can also be formed from carbonates, nitrates, etc.

The efficiency of solution transport (i.e. the analyte transport) into the atomizer (flame, plasma) depends on the rate of aspiration and the efficiency of nebulization. Under constant experimental conditions these factors depend on physical characteristics, such as viscosity, surface tension, vapour pressure, and density of the solution. Since most organic solvents have a lower viscosity and a lower specific mass than water they are more easily aspirated. The surface tension, which is also often substantially lower in organic solvent or oil based matrices, leads to finer nebulization (smaller droplets, smaller particles). This in turn ensures that considerably more sample reaches the atomizer (plasma) per unit time in organic or oil based samples. Moreover, many metal atoms are presumed to be more easily released from organic compounds than from various inorganic compounds, since organic molecules are thermally less stable than inorganic molecules. The higher the proportion of analyte ions aspirated and/or released for detection the higher the ratio of detector signal to analyte concentration. Therefore high quality accurate analysis is only achieved when calibration standard matrix closely matches that of the sample to be analysed.

To calibrate analytical spectroscopic methods for the analysis of water based test samples is relatively easy. Aqueous calibration standard solutions are prepared from well defined and pure starting raw materials (metals, inorganic salts) by dissolving them in water or in mineral acids. The analyte is completely dissolved and is present in water solution usually in an ionic form. When the test sample matrix components are added into the calibration standards, sufficient physical and chemical matching of calibration standards and sample solutions is usually achieved. Aqueous calibration standard solutions are commercially available.

Serious problems arise when aqueous calibration standard solutions are used when attempting to calibrate some so called solid sampling techniques (laser ablation, electrothermal vaporization, slurry nebulization etc.). In these techniques sample analyte enters the atomizer (plasma) in the form of solid particles or is already vaporized. In either case there is a very poor match between aspiration and release mechanisms of the analyte in the aqueous calibration standard and those of the analyte in the sample being tested. However, it has been confirmed experimentally that if the slurry particles are sufficiently small (less than 2 microns), both the analyte transport efficiency of the slurry particle through the sample introduction system and the atomization efficiency of the particle in the plasma are practically identical with those of aqueous calibration solution.

When organic solvents or other organic fluids (e.g. oils) are used for the sample preparation (dissolution), the situation regarding the calibration of atomic spectroscopic techniques is rather complicated. Aqueous calibration standards cannot be evidently used even though there have been many attempts to add aqueous standards into water miscible organic solvents, to prepare water-oil emulsion based standards etc. Standards based on the dissolution of organometallic compounds suffer from the lack of suitable, i.e., well defined, stable, soluble, sufficiently pure, organometallic compounds commercially available. Thus, as starting raw materials synthesized organometallic compounds (metal cyclohexanebutyrates, 2-ethylhexanoates, sulphonates) are used which are only rarely present in real analytical samples. Apart from Conostan®) oil standards, based on petrosulfonates, only a very limited range of elements are covered by commercial standards. As a result, many determinations by atomic spectroscopy methods realized in organic solvents, oils and other organic fluids are not properly calibrated. For example, Conostan® petrochemical based calibration standards are used for the calibration of the determination of many analytes in edible oils and oil standards based on cyclohexanebutyrates are used for the determination of wear metals in used lubricating oils where several analytes are present in the form of relatively large particles of metals or oxides, etc.

SUMMARY

It is an object of the invention to avoid or minimise the disadvantages of the prior art.

According to a first aspect of the invention there is provided the use of nanoparticles comprising an analyte in the preparation of a calibration standard for use in an analytical atomic spectroscopic technique.

According to a second aspect of the invention there is provided a method of calibrating an instrument for use in an analytical atomic spectroscopic method for detecting the presence and/or determining the concentration of an analyte in a medium. The calibration method may include providing a calibration standard comprising nanoparticles including an analyte of known concentration; measuring the concentration of the calibration standard using the instrument to generate a measured concentration for the standard; and adjusting the instrument so the measured concentration is equal to the known concentration.

Analytical atomic spectroscopic techniques include flame and flameless AAS, AES, AFS, ICP-OES, ICP-MS, DCP, XRF and related techniques.

BRIEF DESCRIPTION OF THE DRAWINGS

The foregoing summary and the following detailed description of exemplary embodiments of the present invention may be further understood when read in conjunction with the appended drawings, in which:

FIG. 1 illustrates the ICP-OES response for Example 1;

FIG. 2 illustrates the nitrous oxide-acetylene flame response for Example 2; and FIG. 3 illustrates the ICP-OES response for Example 3.

DETAILED DESCRIPTION OF THE INVENTION

In regards to both aspects of the present invention, the nanoparticles used in herein preferably have an average particle size of from about 0.5 nm to <1,000 nm, or from about 1 nm to about 950 nm, or from about 1 nm to about 500 nm, or from about 1 nm to about 300 nm, or from about 1 nm to about 200 nm, or from about 5 nm to about 200 nm, or from about 5 nm to about 100 nm.

The analyte is preferably an element selected from Groups 1, 2, 3, 4 and 5 of the Periodic Table and from the transition metals and Lanthanides, wherein the element is in solid form at 23 to 25° C.

The analyte may be present in the nanoparticles in substantially pure form or in the form of an oxide or salt thereof, or in the form of an organometallic compound, if appropriate, i.e. where the analyte is a metal.

The analyte is conveniently a metal, optionally in the form of an oxide or salt thereof or in the form of an organometallic compound.

The analyte is preferably selected from Ag, Al, As, B, Ba, Be, Bi, Cd, Ce, Co, Cr, Cu, Fe, In, K, La, Li, Mg, Mn, Mo, Na, Ni, P, Pb, Sb, Si, Sn, Sr, Ti, V, W, Y and Zn, optionally in the form of an oxide or salt thereof or in the form of an organometallic compound.

Suitable salts of the analyte, including those specified immediately above, include chloride, nitrate, sulphate, phosphate, carbonate and silicate. Examples of organometallic compounds include copper and zinc trifluoromethane sulphonates and metal naphthenates. Salts and oxides of the analyte or organometallic compounds are conveniently used when their vaporisation characteristics are better than those of the analyte alone or when the analyte nanoparticles cannot be realised (e.g., for sodium, potassium).

The analyte may be in the form of a solid, e.g., a nanopowder, or it may be dispersed in an aqueous or non-aqueous medium.

Preferred media for dispersing the nanoparticulate analyte include water and non-aqueous media, such as one or more organic solvents and lubricating, mineral or edible oils.

The oils used herein preferably have a viscosity in the range of from about 10 to about 75 cSt at 40° C. as measured by capillary flow viscometry according to ASTM D445-12. Typical properties of such oils are as follows:

|  | 20 BASE OIL | 75 BASE OIL |
|---|---|---|
| Specific Gravity | | |
| (25° C./25° C.) | 0.84-0.86 | 0.86-0.89 |
| Viscosity, cSt | | |
| 40° C.(104° F.) | 14-18 | 65-72 |
| 100° C.(212° F.) | 3-4 | 8.1-8.7 |
| Pour Point, | | |
| ° C.(° F.) | −7(+20) | −15(+5) |
| Flash Point | | |
| ° C.(° F.), minimum | 175(345) | 215(420) |
| Any trace metal | | |
| ppm | <0.10 | <0.15 |

The non-aqueous medium used herein is preferably selected from one or more of benzene, xylene, cyclohexane, hexane, cyclohexanone, methyl isobutyl ketone (MIBK), 2,6-dimethyl-4-heptanone (DIBK)/propan-2-ol mixtures, methylene chloride, kerosene, tetralin (1,2,3,4-tetrahydronaphthalene), tetrahydrofuran/xylene mixtures, toluene, white mineral oils, biodiesel, sunflower oil, soybean oil, and lubricating oils, such as Group I, Group II, Group III, Group IV and Group V base oils, blended lubricating oils and formulated lubricating oils. In the case of oils, white mineral oils such as the 20cSt and 75cSt base oils described above are particularly preferred.

Analytes commonly analysed in lubricating oils include Ag, Al, B, Ba, Cr, Cu, Fe, Mg, Mo, Na, Pb, P, Si, Sn, Ti, V and Zn. Analytes commonly analysed in xylene, white spirit, MIBK and any combination thereof in the petrochemical industry include Ag, Al, As, B, Ba, Be, Bi, Cd, Ce, Co, Cr, Cu, Fe, In, K, La, Li, Mg, Mn, Mo, Na, Ni, P, Pb, Sb, Si, Sn, Sr, Ti, V, W, Y and Zn. Analytes commonly analysed in edible oils include Cd, Cr, Cu, Fe, Pb, Mn and Zn.

When the nanoparticulate analyte is dispersed in a medium, the analyte concentration is preferably in the range of from about 1 mg/kg to about 5,000 mg/kg, more preferably about 1,000 mg/kg.

The analyte nanoparticles herein preferably have a mass in the range of from about $10^{-8}$ pg to about 100 pg, more preferably from about $10^{-6}$ pg to about $10^{-1}$ pg.

The energy required to vaporize a $10^{-3}$ pg analyte nanoparticle is preferably in the range of from about 0.005 to about 1000 pJ, more preferably from about 0.1 to about 200 pJ (pJ=picojoules).

Due to their high surface area and their active bonds, nanoparticles have a tendency to agglomerate and to absorb moisture, oxygen, nitrogen etc. This may result in a number of unwanted side effects, including a larger overall size and a reduced wetting ability during dispersion. To avoid these effects and to minimize agglomeration, dispersing aids, and/or stabilizers and/or surface modifiers may be added to the calibration standard dispersions in order to improve their analytical properties, such as homogeneity and stability. For example, hydrophilic surfactants such as PVP (polyvinylpyrrolidone) or hydrophobic surfactants such as oleic acid may be added.

The nanoparticulate dispersions herein are preferably subjected to mechanical shaking and/or ultrasonication to obtain good homogeneity and stability before any handling (weighing, dilution etc.) of the dispersions.

The calibration standards herein may be used to calibrate instruments used in e.g. the determination of a particular analyte in a wide range of aqueous and organic matrices, such as, for example, in solid sampling, in slurry techniques, in analysis of petroleum fractions, in the determination of wear metals in used lubricating oils, and in the determination of heavy metals in edible oils.

As to the second aspect of the invention there is provided a method of calibrating an instrument for use in an analytical atomic spectroscopic method for detecting the presence and/or determining the concentration of an analyte in a medium, the calibration method comprising using a calibration standard as defined hereinabove containing the analyte of interest, and, if appropriate, diluting the calibration standard in an aqueous or non-aqueous medium to a concentration of from about 1 to about 100 mg/kg.

The calibration method may further comprise the step of dispersing a solid nanoparticulate analyte of interest at the desired analyte concentration to form a calibration standard as defined hereinabove before optionally diluting the calibration standard.

The calibration standard is optionally diluted in any suitable medium. Suitable media include water, one or more organic solvents, such as xylene, toluene or white spirit, and lubricating, mineral or edible oils.

The optionally diluted calibration standard dispersions may contain the analyte in concentrations which are typically about 1-2, 5, 10, 20 and 50 mg/kg for the creation of a calibration curve on the instrument in question.

By way of illustration, a typical embodiment of the invention might be a standard that contains 1000 mg/kg each of B, Ba, Cr, Cu, Fe, Mg, Mo, Na, Pb as nanoparticles dispersed in white mineral oil, such as the 20cSt Base Oil described above. The user may then dilute this standard with, for example, xylene or kerosene, to create a series of working standards of 1-2, 5, 10, 20, 50 mg/kg. These working standards are in turn used to create a calibration curve on the instrument of choice.

Nanoparticles of the analyte or salts and oxides thereof and organometallic compounds are usually synthesized by pyrolytic processes or by wet chemistry and are now commercially available in different forms (nanopowders, dispersions) from a number of producers e.g. SkySpring Nanomaterials, Inc., Nanostructured and Amorphous Materials, Inc., Nanophase Technologies Corp. (all US), MK Nano, Corp. (Canada). Custom manufacturing of nanoparticles in different forms with or without modified surface and in different dispersing media is quite usual. Concentration of the analyte element in nanoparticles must be assayed by wet chemical analysis using primary gravimetric or titrimetric methods.

The calibration standards herein are prepared from starting raw materials composed of nanoparticles. The required amount of these "ready-made" analyte nanoparticles (typically metal or metal oxide nanoparticles) is homogeneously dispersed in a suitable dispersing medium. This medium (liquid) acts as a transport carrier for delivering the solid nanoparticles into the atomizer (flame, ICP source) via a conventional or modified nebulisation system. It is assumed that very small analyte nanoparticles will behave (vaporize, dissociate, atomize) essentially identically to larger analyte particles (dry aerosol) coming into the atomizer from the sprayed standard solution in which the analyte is completely dissolved. Nanoparticles, especially those of low boiling point, have a higher probability of being completely vaporized and atomized during their residence time in the atomizer, particularly in low temperature (2300-3000 K) atomizers (flames). There is also significant experimental evidence that submicron metal (and the majority of metal oxides) particles are quantitatively atomized in the high temperature (6000-8000 K) plasma source.

By preparing calibration standards based on nanoparticulate material, analytical measurements in many analyte-solvent-matrix combinations can be calibrated by means of dispersed inorganic nanoparticles. The limited choice of suitable organometallic compounds is no longer a problem. Moreover, in many cases calibration standards based on nanoparticles fit much better to the analyte form in real samples.

As in the case of conventional calibration standards, there should be close matching of physical and chemical properties between the calibration standards based on nanoparticles and the sample.

Although the use of calibration standards based on nanoparticles might appear to be most advantageous in analytical measurements performed in non-aqueous media, it will be appreciated that the calibration standards herein may also be used as an alternative to conventional standards based on a completely dissolved analyte raw material. For example, aqueous calibration standards prepared from nanoparticles would fit much better to solid sampling techniques, particularly to slurry sampling applications, than conventional standards as modern nanotechnology offers the use of nanoparticles of exactly known average particle size. Similarly, the calibration of the analysis of used lubricating oils would be more accurate using nanoparticle based standards since the sample usually contains solid wear metals particles (e.g. iron, nickel, aluminium), dust particles (silicon oxide) and also lubricating additives nanoparticles (silver, copper).

As indicated above, the analyte nanoparticles herein preferably have a mass in the range of from about $10^{-8}$ pg to about 100 pg, more preferably from about $10^{-6}$ pg to about $10^{-1}$ pg; and the energy required to vaporize a $10^{-3}$ pg analyte nanoparticle is preferably in the range of from about 0.005 to about 1000 pJ, more preferably from about 0.1 to about 200 pJ (pJ=picojoules). These parameters have been calculated for nanoparticles of Al, Mg, Si, Ti, Fe, W, Cu and Cr over a range of particle sizes as set out in the Table below.

Provided the nanoparticle is spherical and has a diameter d, i.e. the radius r=d/2, the volume of the particle is calculated $$V=4/3\ \pi r^3$$

Particle Volume($\mu m^3 \times 10^{-6}$)=(4/3×pi×(particle size/2)^3)/1000

The mass is the calculated by the formula m=V×s, where m is the mass of the particle, V-volume of the particle and s is density of the analyte (metal)

Particle Mass(pg)=(Particle Volume×analyte density)/1,000,000

The energy required for the vaporization of the mass of the analyte nanoparticle (E) is derived from the tabulated value of the vaporization energy of 1 mol of the analyte $$E(J/10^{-3}\ \text{pg})=(\text{Heat of Vaporisation}/\text{Atomic Mass})/1{,}000{,}000{,}000{,}000$$

$$E(\text{picojoule}/10^{-3}\ \text{pg})=1{,}000{,}000{,}000{,}000\times E(J/10^{-3}\ \text{pg})$$

The variables for the Table below may be found e.g. in any of the following documents
1) Any tables of physical properties of metals and ions (also Alfa Aesar Catalogue, American Elements Catalogue of metals and their properties)
2) Pure Appl. Chem. Vol. 81, No. 11, pp. 2131-2156 (2009)
3) Metal Data Tables-Physical properties, Goodfellow Cambridge Ltd. Publication, p. 149, 2012

TABLE

| Particle Size nm | Particle Volume $\mu m^3 \times 10^{-6}$ | Particle Mass pg Al | Particle Mass pg Mg | Particle Mass pg Si | Particle Mass pg Ti | Particle Mass pg Fe | Particle Mass pg W | Particle Mass pg Cu | Particle Mass pg Cr |
|---|---|---|---|---|---|---|---|---|---|
| 5 | 0.0654 | 1.77E−07 | 1.14E−07 | 1.52E−07 | 2.95E−07 | 5.15E−07 | 1.26E−06 | 5.85E−07 | 4.71E−07 |
| 7 | 0.1796 | 4.85E−07 | 3.12E−07 | 4.18E−07 | 8.09E−07 | 1.41E−06 | 3.47E−06 | 1.61E−06 | 1.29E−06 |
| 10 | 0.5236 | 1.41E−06 | 9.10E−07 | 1.22E−06 | 2.36E−06 | 4.12E−06 | 1.01E−05 | 4.68E−06 | 3.76E−06 |
| 15 | 1.7671 | 4.77E−06 | 3.07E−06 | 4.12E−06 | 7.96E−06 | 1.39E−05 | 3.41E−05 | 1.58E−05 | 1.27E−05 |
| 20 | 4.1888 | 1.13E−05 | 7.28E−06 | 9.76E−06 | 1.89E−05 | 3.30E−05 | 8.08E−05 | 3.74E−05 | 3.01E−05 |
| 30 | 14.1372 | 3.82E−05 | 2.46E−05 | 3.29E−05 | 6.37E−05 | 1.11E−04 | 2.73E−04 | 1.26E−04 | 1.02E−04 |
| 40 | 33.5103 | 9.05E−05 | 5.82E−05 | 7.81E−05 | 1.51E−04 | 2.64E−04 | 6.47E−04 | 3.00E−04 | 2.41E−04 |
| 50 | 65.4498 | 1.77E−04 | 1.14E−04 | 1.52E−04 | 2.95E−04 | 5.15E−04 | 1.26E−03 | 5.85E−04 | 4.71E−04 |
| 60 | 113.0973 | 3.05E−04 | 1.97E−04 | 2.64E−04 | 5.10E−04 | 8.90E−04 | 2.18E−03 | 1.01E−03 | 8.13E−04 |
| 70 | 179.5944 | 4.85E−04 | 3.12E−04 | 4.18E−04 | 8.09E−04 | 1.41E−03 | 3.47E−03 | 1.61E−03 | 1.29E−03 |
| 80 | 268.0826 | 7.24E−04 | 4.66E−04 | 6.25E−04 | 1.21E−03 | 2.11E−03 | 5.17E−03 | 2.40E−03 | 1.93E−03 |
| 90 | 381.7035 | 1.03E−03 | 6.63E−04 | 8.89E−04 | 1.72E−03 | 3.00E−03 | 7.37E−03 | 3.41E−03 | 2.74E−03 |
| 100 | 523.5988 | 1.41E−03 | 9.10E−04 | 1.22E−03 | 2.36E−03 | 4.12E−03 | 1.01E−02 | 4.68E−03 | 3.76E−03 |
| 1000 | 523598.7756 | 1.41E+00 | 9.10E−01 | 1.22E+00 | 2.36E+00 | 4.12E+00 | 1.01E+01 | 4.68E+00 | 3.76E+00 |
| Melting Point (° C.) | | 660 | 648.8 | 1410 | 1660 | 1535 | 3410 | 1083.4 | 1857 |
| Boiling point (° C.) | | 2467 | 1090 | 2355 | 3287 | 2750 | 5660 | 2567 | 2672 |
| Density (g/cm$^3$) | | 2.7 | 1.738 | 2.33 | 4.506 | 7.87 | 19.3 | 8.94 | 7.19 |
| Heat of Vaporisation (kJ/mol) | | 317.1 | 147 | 462 | 472 | 416.9 | 846.7 | 339.4 | 397 |
| Atomic Mass (mol) | | 26.98 | 24.31 | 28.09 | 47.87 | 55.85 | 183.84 | 63.55 | 52 |
| E (J/10$^{-3}$ pg) | | 1.18E−11 | 6.05E−12 | 1.64E−11 | 9.86E−12 | 7.46E−12 | 4.61E−12 | 5.34E−12 | 7.63E−12 |
| E(picojoule/10$^{-3}$ pg) | | 11.75 | 6.05 | 16.45 | 9.86 | 7.46 | 4.61 | 5.34 | 7.63 |

E = Energy required to vaporise 10$^{-3}$ pg of the analyte
3.141592654 Pi

The invention is illustrated in the following Examples.

Three trials were carried out, two in oils, viz. CONONSTAN® 20 base oil, and one in a water matrix. The two oil trials were carried out with separate diluent systems, viz. xylene (Example 1) and kerosene (Example 2) to cover the two common sample diluent practices used in oil analysis. The analytical work included analysis by ICP-OES, ICP-MS and Flame-AAS and was carried out in four independent laboratories. Only the applicant's laboratory was aware that nanoparticles had been used to prepare some of the calibration standards.

Example 1

Use of Nanoparticle Standards in the Determination of Copper in Oil by ICP-OES

A sample of copper nanoparticles (5-7 nm) dispersed in organic media, oil-soluble, dispersible, lubricants, additive at a nominal concentration of 500 ppm was sourced from SkySpring Nanomaterials (Catalogue No. 0851 HN). The assay of this material in the applicant's laboratory showed that it contained 110 mg/g by weight copper. The copper content of this solution was independently confirmed by titrimetric analysis at an ISO17025 approved test laboratory. This solution was diluted with CONONSTAN® 20 base oil to create a stock solution of 100 mg/kg Cu. Portions of this stock solution were diluted with xylene to prepare a series of calibration standards of 0, 1, 3, 5, 10 and 20 ppm Cu in xylene. The blank was a 20:80 Conostan 20 base oil:xylene mix. A series of "conventional" calibration standards of the same concentrations were prepared from a 5000 ppm Copper Standard in oil which was sourced from Conostan. The assay of this copper standard was independently tested and certified by an ISO17025 approved test laboratory.

A reference sample of used oil was sourced from SCP Science. This reference material is a sample of material that had been tested by 15 independent accredited laboratories. It had a certified copper content of 3132 ppm. Three test samples of approximately 2, 5 and 10 ppm were prepared from this sample by dilution with the same oil/xylene diluent that was used to make both sets of calibration curves.

A separate independent and ISO 17025 approved laboratory was then engaged to carry out four separate rounds of ICP-OES analysis (a) Calibrate instrument with conventional standards and determine concentration of copper in each of the standards prepared from the nanoparticle suspension.

(b) Calibrate instrument with conventional standards and determine the concentration of copper in the three test oil samples.

(c) Calibrate the instrument with the standards prepared from the nanoparticle suspension and determine the concentration of copper in the three test oil samples.

(d) Repeat round (c) above on the same samples after 17 days.

The results generated from this set of tests confirmed the following:

I. The standards prepared with the copper nanoparticle suspension were efficiently vaporised, atomised and excited in the ICP-OES plasma and provided a linear response with concentration (linear calibration curve shown in FIG. 1).

II. The standards prepared with copper nanoparticles remained stable over the test period.

III. The instrument response for the nanoparticle standards was higher than that for the conventional standards. This indicates that the atomisation of copper from the nanoparticles is more efficient and provides higher sensitivity.

IV. The normal analytical practice of dilution of calibration standards with an oil/xylene diluent also works with calibration standards prepared from a nanoparticle suspension.

Example 2

Use of Nanoparticle Standards in the Determination of Copper in Oil by Atomic Absorption (AA)

The standard and sample preparation outlined in Example 1 above were repeated using an oil/kerosene diluent. The oil was the same as that used in Example 1 and the xylene of Example 1 was replaced by kerosene.

A further independent and ISO 17025 approved laboratory was then engaged to carry out three separate rounds of AA analysis using an acetylene-nitrous oxide flame.
  (a) Calibrate instrument with conventional standards and determine concentration of copper in each of the standards prepared from the nanoparticle suspension.
  (b) Calibrate instrument with conventional standards and determine the concentration of copper in the three test oil samples.
  (c) Calibrate the instrument with the standards prepared from the nanoparticle suspension and determine the concentration of copper in the three test oil samples.

The results generated from this set of tests confirmed the following:
  I. The standards prepared with the copper nanoparticle suspension were efficiently vaporised, atomised and excited in the acetylene-nitrous oxide flame and provided a linear response with concentration (linear calibration curve shown in FIG. 2).
  II. The calibration curves generated using the nanoparticle standards matched those generated with the conventional standards.
  III. The test results for the three oil samples also matched (within normal analytical uncertainty) in each case.
  IV. The normal analytical practice of dilution of calibration standards with an oil/kerosene diluent also works with calibration standards prepared from a nanoparticle suspension.

Example 3

Use of Nanoparticle Standards in the Determination of Iron in Water by ICP

A sample of iron nanoparticles (50-70 nm) suspended in water at a nominal concentration of 500 ppm was sourced from Particular GmbH. The iron content of this solution was independently confirmed by titrimetric analysis at an ISO17025 approved test laboratory.

This iron nanoparticle suspension was used to prepare a series of calibration standards of 0, 2, 5, 10 and 20 ppm Fe. A series of "conventional" calibration standards of the same concentrations were prepared from a 1000 ppm Iron Standard previously tested and certified by an ISO17025 approved test laboratory. Two samples of purified water were then spiked with approximately 5 ppm and ppm iron.

A separate independent and ISO 17025 approved laboratory was then engaged to carry out three separate rounds of ICP-OES analysis
  (a) Calibrate instrument with conventional standards and determine concentration of iron in each of the standards prepared from the nanoparticle suspension.
  (b) Calibrate instrument with conventional standards and determine the concentration of iron in the two spiked water samples.
  (c) Calibrate the instrument with the standards prepared from the nanoparticle suspension and determine the concentration of iron in the two spiked water samples.

This test regime was also completed in-house in the applicant's laboratory using ICP-MS.

The results generated from both set of tests confirmed the following:
  I. On both instruments, ICP-OES and ICP-MS, the calibration curves generated using the nanoparticle standards matched those generated with the conventional standards.
  II. The standards prepared with the iron nanoparticle suspension were efficiently vaporised, atomised and excited in the plasma on both instruments and provided a linear response with concentration (linear calibration curve shown in FIG. 3).
  III. The test results for the two water samples also matched (within normal analytical uncertainty) in each case.

The results generated in both laboratories confirm that aqueous calibration standards prepared with 20-50 nm Fe nanoparticles are effective in the measurement of iron in water based samples by ICP-OES and ICP-MS.

The following abbreviations are used herein:

Flame AAS—atomic absorption spectroscopy using "chemical flames" (air-acetylene flame, nitrous oxide-acetylene flame) as atomizers.

Flameless AAS—atomic absorption spectroscopy using other atomizers (graphite furnace, hydride generation system etc.)

AES—atomic emission spectroscopy

AFS—atomic fluorescence spectroscopy

ICP-OES—optical emission spectroscopy using inductively coupled plasma as an emission source ICP-MS—mass spectroscopy using inductively coupled plasma as an ion (mass) source DCP—direct current plasma (emission source)

XRF—X-ray fluorescence (spectroscopy)

The invention is not limited to the embodiments described herein which may be modified or varied without departing from the scope of the invention as claimed.

The invention claimed is:

1. A method of calibrating an instrument for use in an analytical atomic spectroscopic method for detecting the presence and/or determining the concentration of an analyte in a medium, the calibration method comprising:
  providing a calibration standard comprising nanoparticles including an analyte of known concentration, wherein the analyte is dispersed in a non-aqueous medium selected from one or more organic solvents and lubricating, mineral or edible oils;
  measuring the concentration of the calibration standard using the instrument to generate a measured concentration for the standard; and
  adjusting the instrument so the measured concentration is equal to the known concentration.

2. The method according to claim 1, wherein the nanoparticles have an average particle size of from about 0.5 nm to <1,000 nm.

3. The method according to claim 1, wherein the analyte is an element selected from Groups 1, 2, 3, 4 and 5 of the Periodic Table and from the transition metals and Lanthanides, wherein the element is in solid form at 23 to 25° C.

4. The method according to claim 3, wherein the analyte is present in the nanoparticles in substantially pure form, or in the form of an oxide or salt thereof, or in the form of an organometallic compound.

5. The method according to claim 3, wherein the analyte is a metal, or a metal oxide or salt, or an organometallic compound.

6. The method according to claim 3, wherein the analyte is selected from elements in the group consisting of Ag, Al, As, B, Ba, Be, Bi, Cd, Ce, Co, Cr, Cu, Fe, In, K, La, Li, Mg, Mn, Mo, Na, Ni, P, Pb, Sb, Si, Sn, Sr, Ti, V, W, Y and Zn, or is an oxide or salt of the elements of the group, or is an organometallic compound of the elements of the group.

7. The method according to claim 1, wherein the analyte is in the form of a solid.

8. The method according to claim 1, wherein the medium is selected from one or more of benzene, xylene, cyclohexane, hexane, cyclohexanone, methyl isobutyl ketone (MIBK), 2,6-dimethyl-4-heptanone (DIBK)/propan-2-ol mixtures, methylene chloride, kerosene, tetralin (1,2,3,4-tetrahydronaphthalene), tetrahydrofuran/xylene mixtures, toluene, white mineral oils, biodiesel, sunflower oil, soybean oil, and lubricating oils, Group I, Group II, Group III, Group IV and Group V base oils, blended lubricating oils, and formulated lubricating oils.

9. The method according to claim 1, wherein the analyte is present in the medium in a concentration of from about 1 mg/kg to about 5,000 mg/kg.

10. The method according to claim 1, wherein the analyte nanoparticles have a mass of from about $10^{-8}$ pg to about 100 pg.

11. The method according to claim 1, comprising further diluting the calibration standard in an aqueous or non-aqueous medium to a concentration of from about 1 to about 100 mg/kg.

12. The method according to claim 1, further comprising dispersing a solid nanoparticulate analyte of interest at a desired analyte concentration to form the calibration standard.

13. A method according to claim 1, wherein the calibration standard is further diluted in a medium selected from water, and one or more of organic solvents, xylene, toluene, white spirit, lubricating oils, mineral oils, and edible oils.

* * * * *